(12) United States Patent
Ulvenlund

(10) Patent No.: US 10,857,232 B2
(45) Date of Patent: *Dec. 8, 2020

(54) SURFACTANT COMPOSITION

(71) Applicant: Enza Biotech AB, Lund (SE)

(72) Inventor: Stefan Ulvenlund, Lund (SE)

(73) Assignee: Enza Biotech AB, Lund (SE)

(*) Notice: Subject to any disclaimer, the term of this patent is extended or adjusted under 35 U.S.C. 154(b) by 0 days.

This patent is subject to a terminal disclaimer.

(21) Appl. No.: 16/217,301

(22) Filed: Dec. 12, 2018

(65) Prior Publication Data

US 2019/0201533 A1 Jul. 4, 2019

Related U.S. Application Data

(63) Continuation of application No. 15/025,652, filed as application No. PCT/SE2014/051137 on Sep. 30, 2014, now Pat. No. 10,188,736.

(30) Foreign Application Priority Data

Sep. 30, 2013 (SE) ..................................... 1351143

(51) Int. Cl.
| | | |
|---|---|---|
| *A61K 47/26* | (2006.01) | |
| *C08B 37/00* | (2006.01) | |
| *A61K 8/60* | (2006.01) | |
| *C07H 15/04* | (2006.01) | |
| *C11D 1/66* | (2006.01) | |
| *A61K 8/73* | (2006.01) | |
| *A61Q 19/00* | (2006.01) | |
| *A61K 31/573* | (2006.01) | |
| *A61K 31/58* | (2006.01) | |
| *A61K 8/06* | (2006.01) | |
| *A61K 9/107* | (2006.01) | |
| *A61K 38/28* | (2006.01) | |

(52) U.S. Cl.
CPC ................ *A61K 47/26* (2013.01); *A61K 8/06* (2013.01); *A61K 8/60* (2013.01); *A61K 8/604* (2013.01); *A61K 8/73* (2013.01); *A61K 9/107* (2013.01); *A61K 31/573* (2013.01); *A61K 31/58* (2013.01); *A61K 38/28* (2013.01); *A61Q 19/00* (2013.01); *C07H 15/04* (2013.01); *C08B 37/00* (2013.01); *C11D 1/662* (2013.01); *A61K 2800/10* (2013.01)

(58) Field of Classification Search
None
See application file for complete search history.

(56) References Cited

U.S. PATENT DOCUMENTS

| 5,268,461 A * | 12/1993 | Shoji ...................... C07H 15/04 536/123 |
| 5,734,029 A | 3/1998 | Wulff et al. |
| 6,407,051 B1 | 6/2002 | Smith et al. |
| 8,268,791 B2 | 9/2012 | Maggio |
| 8,455,426 B1 | 6/2013 | Shell et al. |
| 9,254,321 B2 | 2/2016 | Esue et al. |
| 10,188,736 B2 * | 1/2019 | Ulvenlund ............. C11D 1/662 |

FOREIGN PATENT DOCUMENTS

| EP | 0729970 A2 | 9/1996 |
| EP | 08510268 A | 10/1996 |
| EP | 0698079 B1 | 9/1997 |
| EP | 0729970 A3 | 9/1998 |
| EP | 2457580 A1 | 5/2012 |
| JP | 62132531 A | 6/1987 |
| JP | 6469695 A | 3/1989 |
| JP | 01203036 A | 8/1989 |
| JP | 04213398 A | 8/1992 |
| JP | 07215819 A | 8/1995 |
| JP | 09013079 A | 1/1997 |
| JP | 2003522285 A | 7/2003 |
| JP | 2012513412 A | 6/2012 |
| JP | 2013533244 A | 8/2013 |
| WO | 9505159 A1 | 2/1995 |
| WO | 0159059 A1 | 8/2001 |
| WO | 2010097421 A1 | 9/2010 |
| WO | 2010151703 A1 | 12/2010 |

OTHER PUBLICATIONS

"Surfactant Chemistry, Edition 1," written by Gu Jin, Aug. 2008, p. 22, Press of University of Science and Technology of China—with translation.
Extended European Search Report for European Application No. 14 847 605.4, dated Feb. 17, 2017—9 pages.
Final Safety Assessment, "On the Safety Assessment of Alkyl Glyceryl Ethers as used in Cosmetics", Dec. 19, 2011—22 pages.
International Search Report and Written Opinion for International Application No. PCT/SE2014/051137, dated Dec. 23, 2014—10 pages.
Notification of Reasons for Refusal for Japanese Application No. 2016-545722, dated Sep. 25, 2018 with translation—7 pages.
Scudiero et al., "Evaluation of a Soluble Tetrazolium/Formazan Assay for Cell Growth and Drug Sensitivity in Culture using Human and Other Tumor Cell Lines", Cancer Research, 48, Sep. 1, 1988—pp. 4827-4833.
Tween® 80, Sigma Product Information—2 pages.

(Continued)

Primary Examiner — Eric Olson
(74) Attorney, Agent, or Firm — RatnerPrestia

(57) ABSTRACT

A surfactant composition comprises at least one alkylglycoside having the formula $C_nG_m$ wherein C is an alkyl group that is unbranched or branched, saturated or unsaturated, derivatised or non-derivatised, and n is the number of carbon atoms in the alkyl group and is 14 to 24. G is a saccharide residue containing 5 to 6 carbon atoms, and m is a number from 4 to 20. The use and application of the surfactant composition in detergents, emulsifying agents, wetting agents, anti-aggregation and stabilising composition and dispersants comprising the same is also disclosed.

15 Claims, 11 Drawing Sheets

(56) References Cited

OTHER PUBLICATIONS

Ayorinde et al, "Analysis of Some Commercial Polysorbate Formulations using Matrix-assisted Laser Desorption/Ionization Time-of-flight Mass Spectrometry", Rapid Communications in Mass Spectrometry, 2000, 14—pp. 2016-2124.

Bergh et al, "Formation of Formaldehyde and Peroxides by Air Oxidation of High Purity Polyoxyethylene Surfactants", Contact Dermatitis 1998, 39—pp. 14-20.

Ekelund et al, "Correlation between Epithelial Toxicity and Surfactant Structure as Derived from the Effects of Polyethyleneoxide Surfactants on Caco-2 Cell Monolayers and Pig Nasal Mucosa", Journal of Pharmaceutical Sciences, 2005, vol. 94—pp. 730-744.

Ericsson et al, "Effects of Temperature, Salt, and Deuterium Oxide on the Self-aggregation of Alkylglycosides in Dilute Solution. 2. N-Tetradecyl-β-D-maltoside", Langmuir 2005, 21—pp. 1507-1515.

Ericsson et al, "Thermotropic Phase Behaviour of Long-chain Alkylmatosides", Phys. Chem. Chem. Phys. 2005, 7—pp. 2970-2977.

Ericsson, L., "Solid-State Phase Behaviour of Alkylglycosides", Diploma Work, Lund University, 2005—57 pages.

Garcia et al, "Ecological Properties of Alkylglucosides" Chemosphere 1997, vol. 35, No. 3—pp. 545-556.

Hansson, C., "Structure and Thermodynamics of Micellar Alkylmaltoside Solutions", Diploma Work, Lund University, 2001—33 pages.

Jönsson et al, Surfactants and Polymers in Aqueous Solution, Wiley 1998—p. 38.

Mollmann et al, "Displacement of Adsorbed Insulin by Tween 80 Monitored Using Total Internal Reflection Fluorescence and Ellipsometry" Pharmaceutical Research, Nov. 2005, vol. 22, No. 11—pp. 1931-1941.

Reichl et al, "Cell Death Effects of resin-based Dental Material Compounds and Mercurials in Human Gingival Fibroblasts", Archives of Toxicology, 2006, 80(6)—pp. 370-378.

Rosen et al, "The Relationship of the Environmental Effect of Surfactants to Their Interfacial Properties", Journal of Surfactants and Detergents 1999, vol. 2, No. 3, Jul. 1999—pp. 343-347.

Rosen et al, "The Relationship between the Interfacial Properties of Surfactants and Their Toxicity to Aquatic Organisms", Environmental Science and Technology, 2001, vol. 35, No. 5—pp. 954-959.

Svensson et al, "Efficient Synthesis of a Long carbohydrate Chain Alkyl Glycoside Catalyzed by Cyclodextrin Glycosyltransferase (CGTase)", Biotechnolgy and Bioengineering, 2009, vol. 104, No. 5.—pp. 854-861.

Svensson et al, "Enzymatic route to Alkyl Glycosides having Oligomeric Head Groups", Green Chem. 2009, 11—pp. 1222-1226.

Donbrow et al., "Autoxidation of Polysorbates", Journal of Pharmaceutical Sciences, 1978, vol. 67—pp. 1676-1681.

Jönsson et al, "Physicochemical Properties of Surfactants and Polymers Containing Oxyethylene Groups", Surfactants and Polymers in Aqueous Solution, Wiley 1998, p. 91.

Kerwin, B., "Polysorbates 20 and 80 Used in the Formulation of protein Biotherapeutics: Structure and Degradation Pathways", Journal of Pharmaceutical Sciences, 2008, vol. 97, No. 8—pp. 2924-2935.

Eskuchen et al., "Technology and Production of Alkylglycosides", in Alkyl Polyglycosides—Technology,Properties and Applications, 1996, 14 pages.

\* cited by examiner a)

b)

| Surfactant | pH | Storage Temp | Initial | 2 weeks | 4 weeks | 8 weeks | 12 weeks |
|---|---|---|---|---|---|---|---|
| PS20 | 6.8 | 25 | | | | | |
| | | 40 | | ✕ | ✕ | ✕ | ✕ |
| | 7.4 | 25 | | | | | ✕ |
| | | 40 | | ✕ | ✕ | ✕ | ✕ |
| C14G2 | 6.8 | 25 | | ✕ | ✕ | ✕ | ✕ |
| | | 40 | | ✕ | ✕ | ✕ | ✕ |
| | 7.4 | 25 | | ✕ | ✕ | ✕ | ✕ |
| | | 40 | | ✕ | ✕ | ✕ | ✕ |
| A mixture of mainly C16G8, and C16G14 | 6.8 | 25 | | | | | |
| | | 40 | | | ✕ | ✕ | ✕ |
| | 7.4 | 25 | | | | | |
| | | 40 | | | | | |

FIG. 17

SURFACTANT COMPOSITION

This is a Continuation of U.S. patent application Ser. No. 15/025,652, filed Mar. 29, 2016, which is a National Phase Application filed under 35 U.S.C. 371 as a national stage of PCT/SE2014/051137, filed Sep. 30, 2014, an application claiming the benefit from the Swedish Patent Application No. 1351143-1, filed Sep. 30, 2013, the content of each of which is hereby incorporated by reference in its entirety.

TECHNICAL FIELD

The present invention relates to surfactant compositions and their applications.

BACKGROUND

Surfactants (surface active agents, also referred to as tensides) are ubiquitous, and used in products and applications where it is necessary to decrease the surface tension between two immiscible phases, or where it is necessary to increase the solubility of one phase in the other. Normally, one of the phases consists of water or a water-rich mixture (the aqueous phase), whereas the other consists of a liquid or solid phase (the oily phase) that is, by itself, immiscible or poorly soluble in water. Surfactants perform their action by adsorbing to the interface between the aqueous and oily phase, and/or by spontaneously forming aggregates (e.g. liquid crystals or micelles). In order to do so, it is necessary that the surfactant molecule consists of two separate, but linked moieties; a hydrophilic moiety that is soluble in water (the "head-group"), and a hydrophobic moiety, that is soluble in oil (the "tail"). This dual nature of the molecule is referred to as amphiphilicity. The amphiphilic character of the surfactant molecule means that the hydrophilic part will prefer to dwell in the aqueous phase, whereas the hydrophobic part will prefer the oily phase. Consequently, the surfactant as a whole will prefer to reside at the interface between the aqueous and the oily phase, hence decreasing the surface tension between the two phases and facilitating mixing (dispersing) of one phase in the other. Another effect of the surfactant amphiphilicity is its capacity to spontaneously form aggregates. In aqueous solution, soluble surfactants thus spontaneously form aggregates, micelles, where the hydrophobic moieties are directed inwards, away from the aqueous phase, whereas the hydrophilic moieties are directed outwards, towards the aqueous phase. As a consequence, an oily substance can be incorporated in the interior, hydrophobic part of the micelles, hence increasing its solubility. This process is referred to as solubilisation, and the lowest surfactant concentration at which micelles form is referred to as the critical micelle concentration (CMC). The CMC is an important characteristic of a surfactant. Above the CMC all additional surfactants added to the system go to micelles. Before reaching the CMC, the surface tension changes strongly with the concentration of the surfactant. After reaching the CMC, the surface tension remains relatively constant or changes with a lower slope. The value of the CMC for a given agent in a given medium depends on temperature, pressure, and on the presence and concentration of other surface active substances and electrolytes. Another important characteristic of a surfactant is the so-called Krafft temperature. The Krafft temperature is defined as the temperature at which the surfactant concentration of the saturated surfactant solution equals CMC. Consequently, at temperatures below the Krafft temperature, the surfactant solubility is very low and the surfactant behaves as a regular organic molecule. At the Krafft temperature the solubility increases dramatically, micelles form and the surface active properties of the surfactant manifest themselves in a useful manner. At temperatures below the Krafft temperature, on the other hand, the solubility of the surfactant is so low that the surfactant is practically useless in many applications. As will be elaborated on below, most applications therefore require surfactants with Krafft points below room temperature, since products containing surfactants are generally intended for use under everyday conditions.

Both CMC and Krafft temperature depend directly on surfactant structure. Keeping other molecular properties constant, increasing alkyl chain length decreases CMC and favors surfactant adsorption, whereas increasing head-group length decreases the Krafft temperature. This dependence has direct practical consequences for surfactant selection and design. As already described, it is of utmost importance to identify a surfactant that has a Krafft point well below the temperature to which the product will be subjected under actual use (normally room temperature). On the other hand, a long alkyl-chain promotes adsorption and aggregation, so that a smaller concentration of surfactant is required to achieve a given effect. Consequently, a combination of a long alkyl chain with a long head-group is often beneficial for surfactant functionality.

The molecular characteristics of a given surfactant also directly impact its interactions with cells and mucosa, and hence its toxicological properties. In this respect it is important to note that an inherent drawback of the amphiphilic nature of surfactants is their tendency to adsorb to mucosal surfaces and other biointerfaces, as well as to incorporate themselves into cell membranes. Studies show that the toxicity towards aquatic model organisms decreases with decreasing surface activity and increasing size of the head-group [18,19]. These conclusions have been shown to hold true also in human cell models [1]. Furthermore, the studies in human cell models have revealed that a long alkyl chain is also, in itself, beneficial in terms of biocompatibility. Consequently, the combination of a long alkyl chain with a long head-group is beneficial also in terms of toxicity. In more general terms, the toxicological profile of non-ionic (charge-neutral) surfactants are superior as compared with anionic surfactants, which, in turn, are superior over cationic ones [18,19]. For many applications that require high biocompatibility, non-ionic surfactants are therefore the prime choice.

In addition to the aspects pertaining to acute toxicity, the overall environmental impact of a surfactant is also an important factor to consider when comparing different surfactants. Both the properties of the surfactant itself, such as biodegradability, and the properties of the manufacturing process, e.g. the nature of the starting materials, must be considered.

The amphiphilic nature of surfactants makes them act as detergents, wetting agents, emulsifiers, dispersants etc. Surfactants are therefore used in manifold applications, e.g. pharmaceutics, food, paint, adhesives, personal care products, cosmetics, laundry and also for more specialised applications like membrane protein solubilisation.

Dispersions of solid particles in a liquid aqueous medium are normally referred to as suspensions or sols. Such systems are essential in many applications, e.g. pigment particles in paints, and sun-blocking particles in creams and lotions for cosmetic use. In order to properly wet and disperse the particles in suspensions a surfactant is generally required in order to decrease the surface tension between the particle and the continuous medium. Similarly, proper dispersion of a liquid oily phase in water (or dispersion of water in oil) is referred to as emulsification. Again, examples of emulsions include paint and cosmetic preparations.

In the field of pharmaceutics, surfactants are used for e.g. suspension of hydrophobic drug particles in aqueous media, for instance in liquids for inhalation (pulmonary nebulisation and nasal sprays); emulsification of oily drugs in aqueous vehicle, for instance in creams and lotions containing pain-killers; and for inhibition of protein and peptide adsorption and aggregation in liquid formulations for injection and inhalation.

A particularly challenging application is pharmaceutics intended for pulmonary and nasal inhalation (liquids for nebulisation and nasal sprays). In order to have its desired effect, the drug particles in inhaled medications need to be micronised, i.e. milled to a size of a few microns. As a result of the small particle size, the powder becomes extremely cohesive and difficult to disperse. In addition, the drug particles are often very hydrophobic and therefore difficult to wet. As a consequence of these features, aggregation (i.e. formation of larger, composite particles, composed of primary particles) is often encountered. Aggregation is detrimental to product performance, since larger particles do not reach the deep parts of the pulmonary tract, due to impaction and concomitant retention in airway bifurcations. Due to the challenging demands on formulations for inhalation, it is generally true that a formulation concept that works in the area of inhalation also works in other, less challenging pharmaceutical areas, such as dispersion of solid particles in topical creams and lotions as well as injectabilia.

Preferably, a surfactant is chemically stable, i.e. does not readily degrade under the intended product shelf life and does not induce degradation of other components in the formulation. This is especially important for pharmaceutics, cosmetics and food, where a strict minimisation of degradents is desirable for reason of safety and product performance.

Today, the field of non-ionic surfactants is completely dominated by substances based on the use of polyethyleneglycole (PEG, also referred to as polyethyleneoxide, PEO) as hydrophilic head-group. In simple PEG-chain surfactants, the PEG chain may be attached to the hydrophobic moiety of the surfactant (the alkyl chain) trough an ester bond (e.g. Solutol™ and the Myrj™ family of surfactants) or an ether bond (e.g. the Brij™ family of surfactants). More complex PEG-based surfactants include the well-known family of ethoxylated sorbitan esters known as polysorbates (or Tween™), amphiphilic co-polymers of PEG and poly (propylene oxide) (e.g. Pluronics™), and ethoxylated triglycerides (e.g. Cremophor™). Polysorbate is of particular interest, since it is the only surfactant currently approved for all pharmaceutical administration forms.

In spite of the fact that they are produced and used on an enormous scale, all surfactants based on PEG share a number of substantial drawbacks, namely formation of toxic degradation products in aqueous systems (e.g. formaldehyde, formic acid and acetaldehyde); chemical instability and generation of oxidising peroxo radicals having a detrimental effect on product stability; polydispersity and batch variability [2-5].

Furthermore, the temperature-sensitivity of aqueous solutions (phase separation, clouding, emulsification failure) is a problem in processes that involve heat, such as e.g. sterilisation by means of autoclavation [6]. In addition, most PEG-based surfactants have petrochemical origin, thus not originating from renewable sources, which is important when considering the environmental impact of a surfactant.

Another group of non-ionic surfactants are the alkylglycosides, also named alkylpolyglucosides, which are non-ionic surfactants derived from saccharides (sugars). These surfactants have been found to be compatible with skin and mucosa and to be non-toxic in acute and repeated dose toxicity studies [20]. Glycosides are substituted saccharides in which the substituent group is attached, through an oxygen atom, to an aldehyde or ketone carbon. Accordingly, glycosides are considered acetals. As with the term "saccharide", the term "glycoside" defines neither the number nor the identity of the saccharide units in the molecule. A common shorthand nomenclature applied to alkylglycosides is $C_nG_m$, where n is defined as the number of carbon atoms in the alkyl chain and m the number of saccharide units (normally glucose units) comprising the head group.

Alkylglycosides are known to be effective as surfactants in detergents and they exhibit solubilizing properties. In addition, alkylglycosides have a favourable biodegradability, with degradation products being an alcohol or fatty acid and an oligosaccharide [23]. In contrast to the PEG-based surfactants they are stable towards hydrolysis and autoxidation in aqueous systems, and do not give rise to toxic degradation products, Hence, they have found use in many applications where they come in contact with the human body, such as cosmetics and personal care products. Examples of alkylglycosides used today in these applications are EcoSense 1200 (alkylpoly glucoside C12-14) and EcoSense 919 (alkylpoly glucoside C8-16) from Dow Chemicals, Plantaren (decyl glucoside), Plantapon LGC Sorb (sodium lauryl glucose carboxylate), Plantasol CCG (caprylyl capryl glucoside) from Cognis, and TEGO Care CG90 (C16-C18 glucoside) from Evonik, etc. In the pharmaceutical field, Aegis Therapeutics has recently developed technologies primarily utilizing C14G2 for enhancement of the physical stability and bioavailability of peptides and proteins [21,22].

Ways to produce alkylglycosides have previously been disclosed [8,9,10].

Conventional, commercially available alkylglycosides, such as those mentioned in the preceding paragraph, address many of the issues related to PEG-based surfactants, but still have a number of drawbacks. Conventional Fischer synthesis, used for the industrial production of these alkylglycosides, yields a polydisperse mixture of alkylglycosides having only 1-3 repeating sugar units [7]. With such short head-groups, it is not possible to extend the length of the tail without risking problems related to high Krafft points and concomitant issues related to poor solubility. As already described, the toxicity of a surfactant also increases with shorter head-group. Hence, there is a need for a new type of surfactant that addresses these issues.

SUMMARY OF THE INVENTION

We have found that alkylglycosides $C_nG_m$ with a long alkyl chain (n≥14) and long head-group (m≥4) indeed address these needs and also bring other, unexpected benefits in terms of surfactant functionality. These novel alkylglycosides according to the present invention can be produced by enzymatic means. Production of alkylglycosides using enzymes has previously been disclosed in EP2401389A1. According to the present invention, depending on the choice of enzyme and reactants, the resulting alkylglycoside composition may have either of the following two key characteristics:

(A). A binary mixture of $C_nG_{m1}$ and $C_nG_{m2}$, where m1 and m2 is either 7 and 13, or 8 and 14. In the following, this type of binary surfactant composition is referred to by the shorthand notation $C_nG_{m1/m2}$. Thus, $C_nG_{7/13}$ refers to a binary mixture of $C_nG_7$ and $C_nG_{13}$, whereas $C_nG_{8/14}$ refers to a binary mixture of $C_nG_8$ and $C_nG_{14}$. For instance, this type of binary mixtures can be produced using commercially available $C_{16}G_2$ as starting material, which yields $C_{16}G_{8/14}$.

(B). A mixture of molecules $C_nG_4, C_nG_5, \ldots, C_nG_{20}$. In the following, this type of polydisperse surfactant composition is referred to by the shorthand notation $C_nG_{4-20}$. Thus, $C_{16}G_{4-20}$ refers to a mixture of $C_{16}G_n$ molecules with n in the range 4-20. For instance, this type of polydisperse mixture can be produced from a commercially available mixture of $C_{16}G_1$ and $C_{18}G_1$ (brand name TEGO Care CG16 from Evonik), which yields $C_{16-18}G_{4-20}$.

The present invention relates to unique surfactant compositions based on alkylglycosides with hydrophilic headgroups consisting of four or more repeating saccharide units. In contrast to existing alkylglycoside compositions, the composition described herein contains alkylglycosides with long head-groups (n≥14) as main components. The invention also relates to the use of the compositions as surface-active agents particularly in the field of wetting particles and surfaces, emulsification and stabilisation of pharmaceuticals.

The above mentioned problems described in the Background are solved with the surfactant compositions according to the present invention.

According to one object the present invention relates to a surfactant composition comprising at least one alkylglycoside having the formula I $$C_nG_m \qquad (I)$$

wherein
C is an alkyl group;
n is the number of carbon atoms in the alkyl group and is 14 to 24;
said alkyl group being unbranched or branched, saturated or unsaturated, derivatised or non-derivatised;
G is a saccharide unit containing 5 to 6 carbon atoms; and
m is a number from 4 to 20.

According to one embodiment the alkyl group comprises cyclic fractions.

According to one embodiment m is 4-19, preferably 4-18, preferably 4-17, preferably 4-16, preferably 4-15, or preferably 4-14.

According to another embodiment m is between 6 and 18, preferably between 7 and 17, more preferably is chosen from 7, 8, 13 or 14.

According to another embodiment n is 14 to 22, preferably 14 to 20, preferably 14 to 18, and more preferably 16 to 18.

According to another embodiment m is selected from 7, 8, 13, or 14; and n is selected from 16 or 18.

According to another embodiment the surfactant composition comprises at least two alkylglycosides having m being 7 or 8 and 13 or 14, respectively.

According to another embodiment the ratio between $(C_nG_8)$ to $(C_nG_{14})$ or $(C_nG_7)$ to $(C_nG_{13})$ is about 50:50 to 95:5.

Polydisperse mixtures comprising these alkylglycosides are referred to as $C_nG_{4-20}$, in accordance with the nomenclature and definitions described previously. Preferred embodiments of a polydisperse mixture may be disclosed as e.g. $C_nG_{4-19}$, $C_nG_{4-18}$ etc, in accordance with the above mentioned embodiments.

Binary mixtures consistent with the above mentioned preferred embodiments may be referred to as e.g. $C_nG_{8/14}$ and $C_nG_{7/13}$, respectively, in accordance with the nomenclature and definitions described previously.

Naturally other types of binary combinations may also be made within the scope of the present invention.

According to another embodiment the at least one alkylglycoside has a surface tension value at or above critical micelle concentration (CMC) of at least 32 mN/m, for example at least 40 mN/m, preferably 42-49 mN/m, preferably about 45-49 mN/m, such as about 47 mN/m.

According to one object the present invention relates to a detergent composition comprising said surfactant composition.

According to one object the present invention relates to a wetting agent comprising said surfactant composition.

According to one object the present invention relates to an emulsifying agent comprising said surfactant composition.

According to one object the present invention relates to a dispersant composition comprising said surfactant composition.

According to one object the present invention relates to an anti-aggregation and stabilising composition comprising biomolecules and said surfactant composition.

According to one object the present invention relates to use of said surfactant composition as a detergent, a wetting agent, an emulsifying agent, an anti-aggregation agent or a dispersant.

According to one object the present invention relates to use of said surfactant composition in foods, beverages, pharmaceuticals, cosmetics, personal care products, detergents or cleaning agents.

BRIEF DESCRIPTION OF THE DRAWINGS

FIG. 3 shows the total BHT content as a function of time in systems stored at 40° C. Solid squares denote the system in which a surfactant composition comprising a $C_{16}G_{8/14}$ mixture was used as dispersant, whereas open circles and triangles denote systems containing polysorbate of super-refined and pharma grade, respectively. The error bars represent 1a.

FIG. 17 shows a table with results from a study investigating the ability of Polysorbate 20, C14G2 and a $C_{16}G_{8/14}$ mixture to inhibit precipitation of insulin, where filled boxes denote systems in which a solid precipitate was observed after a given time of storage under the conditions indicated.

DETAILED DESCRIPTION

Figure 1:
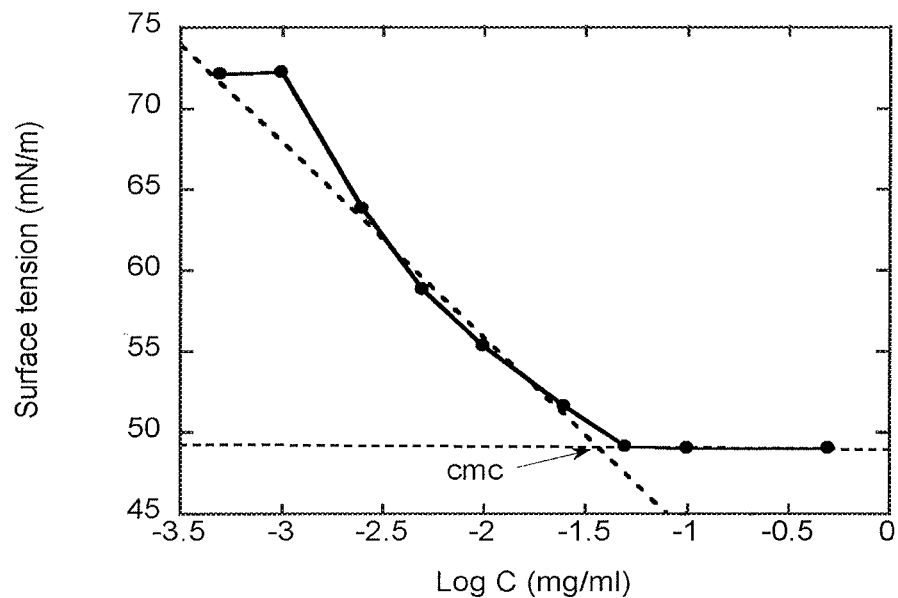
FIG. 1 illustrates the tensiometric determination of the CMC of a surfactant composition comprising a $C_{16}G_{8/14}$ mixture at room temperature.

The present invention relates to unique surfactant compositions based on alkylglycosides with hydrophilic headgroups consisting of four or more repeating saccharide units. In contrast to existing alkylglycoside compositions, the composition described herein contains alkylglycosides with long head-groups (n≥4) as main components. The invention also relates to the use of the compositions as surface-active agents particularly in the field of wetting particles and surfaces, emulsification and stabilisation of pharmaceuticals.

Disclosed herein is a surfactant composition comprising at least one alkylglycoside which has the formula I $$C_nG_m \qquad (I)$$

wherein
C is an alkyl group;
n is the number of carbon atoms in the alkyl group and is 14 to 24;
said alkyl group being unbranched or branched, saturated or unsaturated, derivatised or non-derivatised;
G is a saccharide unit containing 5 to 6 carbon atoms; and
m is a number from 4 to 20.

The alkyl moiety (C in formula I) of the alkylglycosides present in the surfactant composition according to the invention also emanates preferably from readily available derivatives of renewable raw materials, more particularly from fatty alcohols, although branched-chain isomers thereof may also be used for the production of suitable alkylglycosides. Accordingly, primary alcohols containing unbranched groups in the range C14-C20 and mixtures thereof are particularly useful. The alkyl group may contain from 16 to 20 carbon atoms (n=16-20).

Particularly preferred surfactant compositions have alkylglycosides having n being 16 or 18, such as hexadecyl (straight saturated chain) or oleoyl (straight, unsaturated), or 12-hydroxystearoyl (straight, derivatised), or any combination thereof.

However, the index n may preferably be chosen from 14-22, 14-20, or 16-18.

G (the head-group) in the formula is a repeating saccharide unit. The structure of the residue being determined by the mono, di, or oligosaccharide used as starting material. Examples of the starting material for G include e.g. monosaccharides as glucose, fructose, galactose, xylose, mannose, lyxose, arabinose, and mixtures of these, and oligosaccharides as maltose, xylobiose, isomaltose, cellobiose, gentiobiose, lactose, sucrose, nigerose, turanose, raffinose, gentianose, melezitos, and mixtures of these. Particularly preferred is glucose.

The index m in the formula is a number from 4 to 20, which represents the so-called degree of oligomerisation, i.e. the number of repeating saccharide units. The index m may be chosen from 4-19, 4-18, 4-17, 4-16, 4-15, or 4-14. The index m may alternatively be between 5 and 20, e.g. 5-19, 5-18, 5-17, 5-16, 5-15, or 5-14. The index m may alternatively be between 6 and 18, such as 7 and 17, and may e.g. be chosen from 7, 8, 9, 10, 11, 12, 13 or 14, more preferably chosen from 7, 8, 13 or 14.

If the surfactant composition according to the present invention however contains alkylglykosides outside the desirable range according to the present invention, these may then, if present in too high amounts, contribute with a less efficient effect and thus less desirable effect of the surfactant composition. It would be preferable that the present invention did not contain any alkylglycoside chosen from $G_{1\text{-}3}$. However, if there is any alkylglycoside chosen from $G_{1\text{-}3}$ present in said composition, it would be preferable to limit the amount to at most 33% of the alkylglycosides. Thus, according to one embodiment the relationship between $G_{1\text{-}3}$ and $G_{4\text{-}20}$ is preferably at most 33:67, preferably at most 30:70, preferably at most 20:80, preferably at most 20:90 and preferably at most 5:95.

The longer head-group makes the surfactant composition less active as an irritant on skin and mucosa, and more benign to living cells. In other words, the longer head-group increases biocompatibility.

Particularly preferred alkylglycosides are such that they either
(1) contain at least one or a mixture of alkylglycosides having m being selected from 7 to 14, preferably comprising $C_nG_7$ or $C_nG_8$. Mixtures may e.g. contain $(C_nG_7)$ and $(C_nG_{13})$, or $(C_nG_8)$ and $(C_nG_{14})$.

(2) contain a polydisperse mixture of components $C_nG_m$, having components with m=4-20 preferably representing at least 67% of the total amount of alkylglycosides present.

As an example the surfactant composition may comprise at least two alkylglycosides which have m being 7 or 8, and 13 or 14, respectively, and preferably are chosen from $C_{16}G_7$, $C_{16}G_8$, $C_{16}G_{13}$ and $C_{16}G_{14}$, where $C_{16}$ denotes a hexadecyl residue.

As another example, the surfactant composition may consist of a polydisperse mixture of G16Gn alkylglycosides. If such mixture comprises any $C_{16}G_1$, $C_{16}G_2$ and $C_{16}G_3$ they preferably together represent at most 33% of the mixture.

As a further example the surfactant composition may comprise at least two alkylglycosides which have m being 7 or 8 and 13 or 14, respectively, and preferably are chosen from C18G7, C18G8, C18G13 and C18G14, and preferably C18 denotes an oleoyl residue or an 12-hydroxystearoyl residue.

The ratio of CnG8 to CnG14, or CnG7 to CnG13, may be between 50:50 to 95:5, such as 50:50 to 90:10.

G is covalently linked via a glycosidic bond to a single alkyl chain containing at least fourteen carbons. This class of surfactant compositions comprise head-groups that are longer than those present in alkylglycoside products available today. Thus, surfactant compositions according to the present invention address severe drawbacks of the current technology, in the following ways: By making the head-group significantly longer than is the case in current technology, the Krafft point for a given length of alkyl chain decreases, hence increasing solubility at temperatures relevant for most applications. Since many applications require or benefit from long alkyl chains, this opens up the possibility to replace current technology with surfactant compositions according to the present invention that are much more efficient, thus decreasing the amount required in any given application. A longer head-group also decreases the toxicity of the alkylglycoside, and lowers its tendency to act as an irritant on mucosa and other sensitive tissue.

The alkylglycosides according to the present invention exhibit high chemical stability. In addition, the surfactant composition according to the present invention may be subjected to heat without losing its properties as an excellent surfactant composition. The present invention thus provides an excellent surfactant composition that combines a low Krafft point with high efficiency, high physical and chemical stability and low toxicity.

According to another embodiment, the surfactant composition consists of one alkylglycoside according to formula I.

At concentrations above the critical micelle concentration (CMC), the present surfactant composition may show surface tension values at or above CMC of at least 32 mN/m, for example at least 40 mN/m, preferably at least 45 mN/m, such as about 42-53 mN/m, about 45-51 mN/m and about 49 mN/m.

It has been discovered that the present surfactant composition displays a very surprising behavior in terms of the relationship between its surface activity (as defined by the surface tension at the air-water interface) and its wetting properties. More specifically, the high surface tension suggest a much lower surface activity than for existing alkylglycosides and ethoxylated surfactants (e.g. polysorbate 80), yet its wetting properties are superior. The surfactant composition also packs in a surprisingly efficient manner when adsorbed to surfaces, which contributes beneficially to its superior wetting and emulsification properties.

The present surfactant composition may thus be used for efficient wetting of surfaces or particles, emulsification of water/oil systems, prevention of unwanted intermolecular interaction between proteins and peptides (aggregation) and/or between said molecules and surfaces in their environment (adsorption). The present surfactant composition and solutions thereof are heat-stable and stable when subjected to freezing and/or thawing.

The surfactant composition is capable of providing excellent wetting and dispersion of particles of hydrophobic small organic molecules used in pharmaceutical formulations. The surfactant composition may also be used as an emulsifier providing for an emulsion. It may also be used for increasing the stability, reduce aggregation and immunogenicity and increase biological activity of peptides and proteins in therapeutically useful formulations.

Thus, the surfactant composition according to the invention may be comprised in a detergent composition, a wetting agent, an emulsifying agent or in a dispersant composition.

It has been discovered that using surfactant compositions according to the present invention, compositions comprising alkylglycosides having at least four saccharide units result in improvement in the wetting properties of aqueous solutions of said alkylglycosides. Also, it has been surprisingly found that the use of alkylglycoside compositions according to the present invention, to a higher extent reduces, prevents, or lessens peptide or protein association or aggregation of an emulsion or suspension or mixture. For example, the peptide or protein self-association or self-aggregation is reduced. Also, the association or aggregation with other peptides or proteins when administered to the subject is reduced.

Furthermore, the present surfactant composition may be used in foods, beverages, pharmaceuticals, cosmetics, personal care products, detergents, cleaning agents, etc. Examples are gels, creams, lotions, tooth paste, ointments, injectabilia, nasal sprays, liquids for inhalation, eye drops, tablets, laundry detergents, wet wipes, etc.

Examples

Thermal Physical Stability, Solubility and Krafft Point

Over the course of extensive studies, solutions comprising a $C_{16}G_{8/14}$ mixture were found never to produce any precipitate, not even when stored under refrigerated conditions (2° C.) for years. This means that the Krafft point of both $C_{16}G_8$ and $C_{16}G_{14}$ is below 2° C. This value is compared with other alkylglycosides [11,12,13] in Table 1. Similarly, polydisperse mixtures of $C_{16-18}G_{4-20}$ were found to be soluble at room temperature, and not to produce a precipitate when stored under refrigerated conditions for extended periods of time (Table 1).

Figure 16:
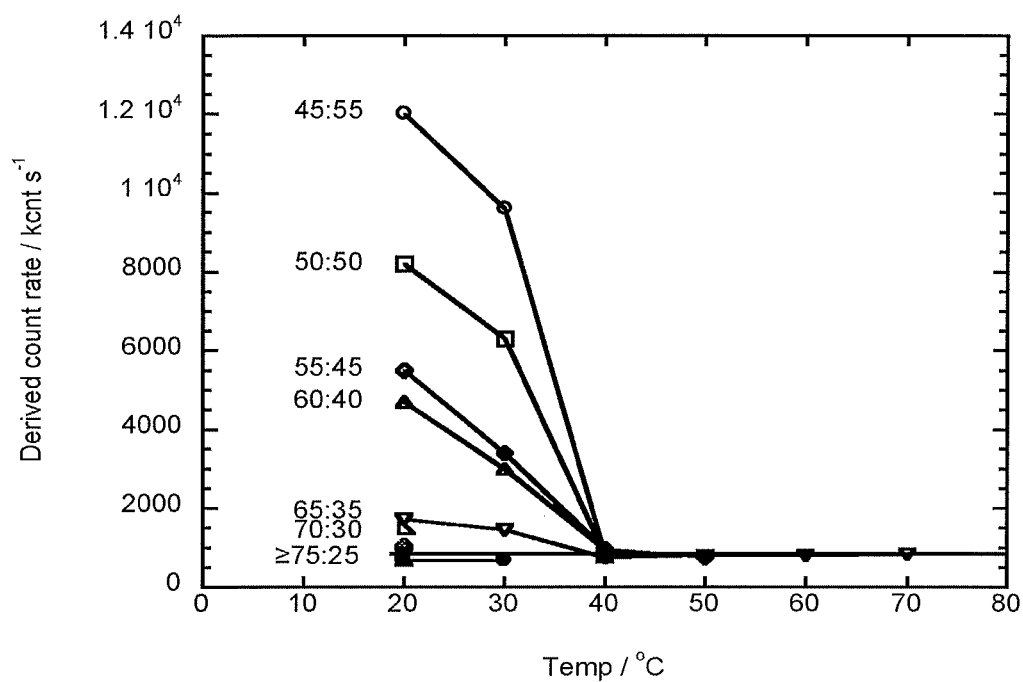
FIG. 16 shows light scattering data from aqueous solutions of mixtures of $C_{16\text{-}18}G_{4\text{-}20}$ and $C_{16\text{-}18}G_{1\text{-}3}$. The total surfactant concentration was 2 mg/ml in all experiments, and the $C_{16\text{-}18}G_{4\text{-}20}$ to $C_{16\text{-}18}G_{1\text{-}3}$ ratio is indicated in the figure. The y axis of the figure gives the turbidity of the samples, stated as the number of photons reaching the detector per unit time (referred to as "derived count rate" and given in units of kilo-counts per second).

In order to determine the Krafft point of a $C_{16-18}G_{1-20}$ mixture as a function of the average head-group length, the following experiment was conducted: By chromatography, $C_{16-18}G_{1-20}$ was split into two fractions: $C_{16-18}G_{1-3}$ and $C_{16-18}G_{4-20}$. The Krafft temperature of each fraction was determined and found to be 35-40° C. and <2° C., respectively (Table 1). Next, $C_{16-18}G_{1-3}$ was blended into $C_{16-18}G_{4-20}$ in increasing amounts, and the Krafft point determined by light scattering experiments for each specific mixture. The results are summarised in FIG. 16. As is evident, the light scattering intensity is constant and very low for compositions such that the $C_{16-18}G_{4-20}$: $C_{16-18}G_{1-3}$ ratio is 75:25. This shows that all material is properly dissolved, and hence that the Krafft temperature is below room temperature. However, for $C_{16-18}G_{4-20}$: $C_{16-18}G_{1-3}$ ratios 70:30, the systems need to be heated to 30-40° C. before the light scattering intensity is consistent with a properly dissolved system. Hence, the data in FIG. 16 clearly demonstrate that $C_{16-18}G_{1-20}$ mixtures have cloud point above room temperatures if the short-chain fraction ($C_{16-18}G_{1-3}$) comprises more than 30% of the alkylglycoside composition. As is evident from these studies, enlongation of the head-group dramatically decreases the Krafft point and enables longer alkyl chains to be used without sacrificing solubility.

In contrast to the case of PEG-based surfactants, heating of solutions comprising a $C_{16}G_{8/14}$ mixture have been found not to produce phase separation, even at the boiling point.

TABLE 1

Krafft point of selected alkylglycosides.

| Surfactant | Krafft point/° C. | Reference |
|---|---|---|
| $C_{16}G_{8/14}$ | <2 | Measured for present application |
| $C_{16}G_2$ | 41 | [12] |
| $C_{14}G_2$ | 32 | [11] |
| $C_{12}G_{8/14}$ | <2 | Measured for present application |
| $C_{12}G_2$ | <0 | [11] |
| $C_{12}G_1$ | 38 | [13] |
| $C_{16-18}G_{4-20}$ | <2 | Measured for present application |
| $C_{16-18}G_{1-3}$ | 35-40 | Measured for present application |
| $C_{16-18}G_1$ (TEGO Care CG90) | >90 | Measured for present application |

CMC and Surface Tension at the Air-Water Interface

The CMC of a surfactant composition comprising a $C_{16}G_{8/14}$ mixture was determined by means of tensiometry (FIG. 1). According to the measurement, the CMC is 37 mg/L, which for this particular mixture is equivalent to 24 μM. This value may be compared to the corresponding value for the PEG-based surfactants $C_{16}E_9$, $C_{16}E_{12}$ and $C_{16}E_{21}$ which show CMC values of 2.1, 2.3 and 3.9 μM, respectively [14]. The value may also be compared with the CMC of Polysorbate 80, at 13-15 mg/L (10-11 μM) [15]. These results confirm that a surfactant composition comprising a $C_{16}G_{8/14}$ mixture is more hydrophilic, compared to similar PEG-based surfactants. Surprisingly, it has been found that the surface tension of solutions of comprising a $C_{16}G_{8/14}$ mixture at concentrations above the CMC (49 mN/m) is significantly higher than that of PEG-based surfactants (30-35 mN/m), and that of conventional alkylglycosides with short head-group (32-37 mN/m) [16]. The high surface tension may be a key to the biocompatibility of the $C_{16}G_{8/14}$ mixture.

Adsorption to Hydrophobic Surfaces

Figure 2:
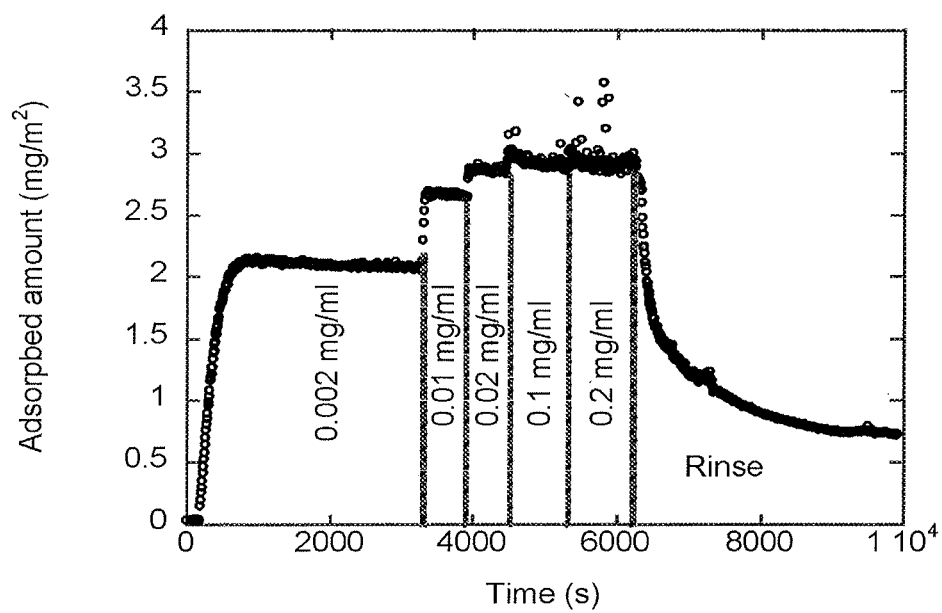
FIG. 2 shows ellipsometric data on the adsorbed amount of a surfactant composition comprising a $C_{16}G_{8/14}$ mixture on hydrophobic substrate (silica, hydrophobized with dimethyloctylchlorosilane). The concentration of the $C_{16}G_{8/14}$ solution in each phase of the experiment is displayed in the figure.
Figure 3:
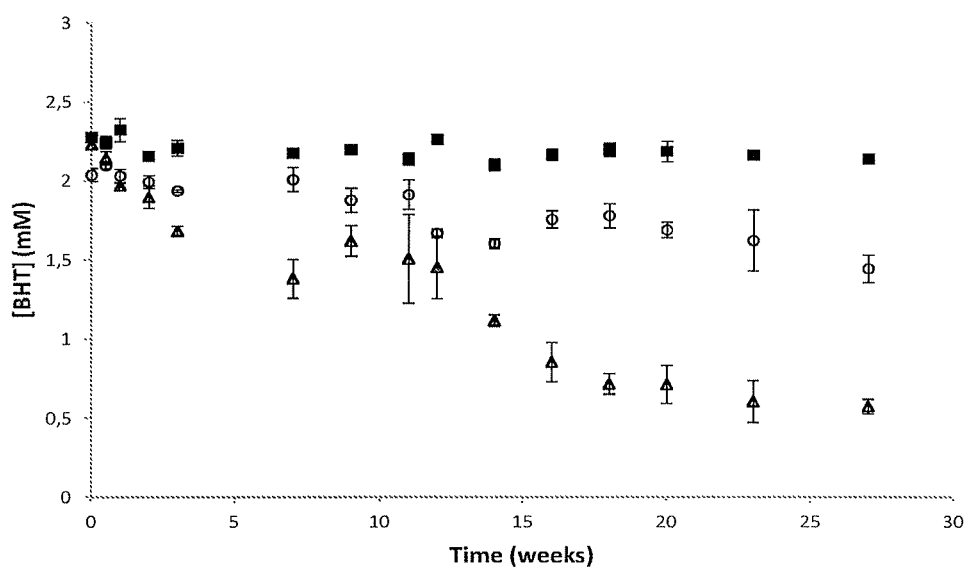

Ellipsometric studies of the adsorption of a $C_{16}G_{8/14}$ mixture to hydrophobic model surfaces reveal a very efficient surface coverage, corresponding to 3 mg/m² (2 μmol/m²), FIG. 2. For comparison, the adsorption of Polysorbate 80 to hydrophobic silica substrates is 1.4 mg/m² (1.1 μmol/m²) at 0.028 mg/ml [17]. Hence, in terms of adsorbed mass, $C_{16}G_{8/14}$ is about twice as efficient as Polysorbate 80, in spite of its lower surface activity (as determined by tensiometry; see above).

Cell Toxicity

The cytotoxicity of a surfactant composition comprising a $C_{16}G_{8/14}$ mixture was evaluated and compared with a number of other surfactants at concentrations above and below the critical micelle concentration (CMC). As parameter for cytotoxicity, cell metabolism was assessed by XTT conversion. The XTT assay is based on the mitochondrial activity of the cells and reflects on how active and thereby how viable the cells are [24,25]. The XTT compound (sodium 3'[1-phenyl-aminocarbonyl]-3,4-tetrazolium bis[4-methoxy-6-nitro] benzene sulphonic acid hydrate) is reduced by the mitochondria and forms an orange coloured formazan dye. The colour change from yellow to orange is measured by a spectrophotometer at 450 nm.

Figure 15:
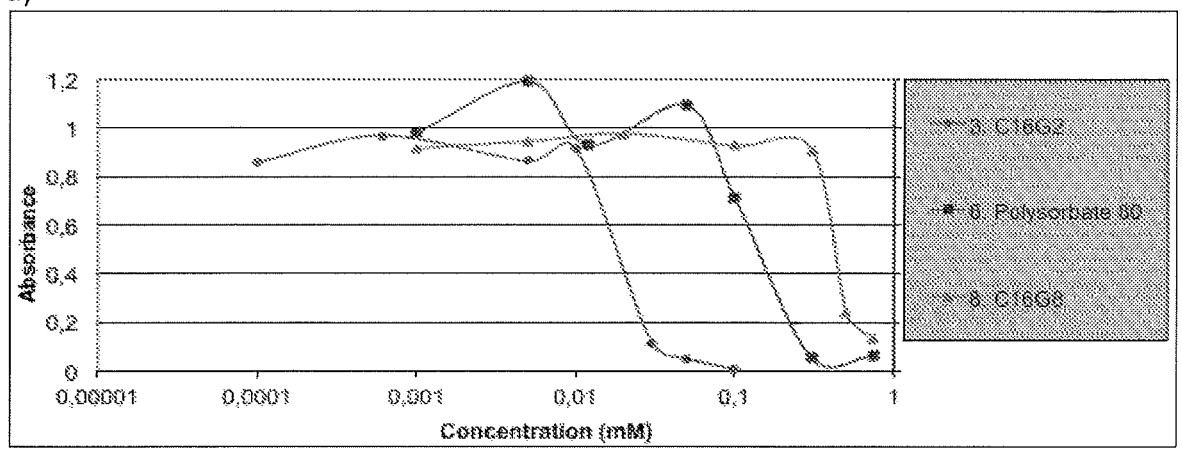
FIG. 15 shows the results from the cell toxicity study using fibroblasts as model cells.
Figure 15:
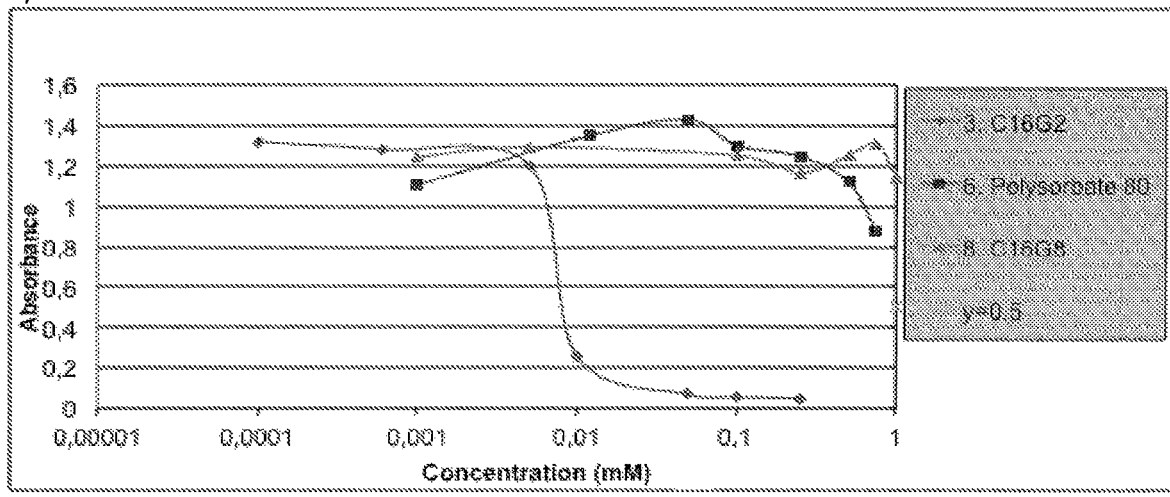

Fibroblasts cells seeded in 96-well plates at a cell concentration within the linear region for the XTT assay were cultured for 24 hours in 200 μl Dulbecco's modified Eagles's medium (DMEM) containing 10% fetal bovine serum (FBS) prior to the addition of the surfactants. The culture medium was then removed and 200 μl of the respective surfactant solutions was added to the wells and incubated for 1 hour. The surfactant solution was removed and 200 μl XTT medium was added to the wells, including blanks, and incubated for 2 hours (37° C., 5% $CO_2$). The absorbance was measured at 450 nm. The results were expressed as absorbance observed as % of control cultures (non-treated cells). As can be seen in FIG. 15*a* the cell viability is higher in the composition of $C_{16}G_{8/14}$ (denoted C16G8 in figure) than in both polysorbate 80 and C16G2. The concentration at which the cell viability was decreased by 50% (IC50) was 0.43 mM for the $C_{16}G_{8/14}$ composition compared to 0.13 mM for polysorbate 80 and 0.017 mM for C16G2.

After the surfactant composition was removed, the cells that had been exposed to the $C_{16}G_{8/14}$ mixture had completely recovered after 2 hours (FIG. 15*b*) while a slightly less complete recovery was observed for polysorbate 80. The cells that had been exposed to C16G2 on the other hand, did not recover at all during 2 hours.

Chemical Stability

Figure 4:
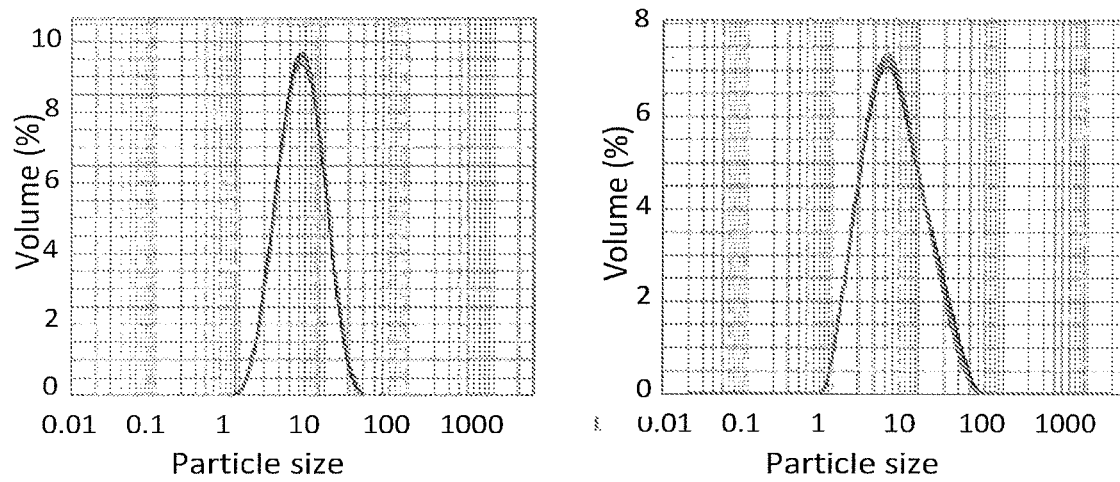
FIG. 4 shows data on particle size distributions of BDP dispersed by high-shear mixing in aqueous vehicles comprising a $C_{16}G_{8/14}$ mixture (left hand panel), or comprising PS80 (right hand panel).

The chemical stability of a $C_{16}G_{8/14}$ mixture in an aqueous formulation sensitive to oxidation was compared to that of two different grades of Polysorbate 80 (Super-Refined and Pharma Grade). Butylated hydroxytoluene (BHT) was used as oxidation-prone model compound. BHT is easily oxidised to 3,3',5,5'-tetra-bis-(tert-butyl)-stilbenequinone, which is bright yellow. 0.5 mg/ml of micronised BHT was dispersed in 150 mM NaCl solution, using 0.2 mg/ml of surfactant as dispersant. The preparations were placed on stability at room temperature and 40° C. The formulations were analysed by HPLC and visually inspected at regular time points. During the course of the study, the visual inspection of the bottles revealed that gradual yellow discoloration was much more pronounced for the solutions containing polysorbate, which clearly indicated a lower chemical stability of polysorbate than the $C_{16}G_{8/14}$ mixture. The HPLC results provide quantitative conformation of this conclusion, as displayed in FIG. 4. As is evident, a $C_{16}G_{8/14}$ mixture is vastly superior to the two grades of polysorbate in terms of chemical stability of the formulation. In actual fact, over the course of the 28-week study, the BHT content in the $C_{16}G_{8/14}$ mixture system did not decrease, even under accelerated conditions (40° C.). In the polysorbate systems, on the other hand, BHT content was found to decrease dramatically with time.

Inhibition of Peptide and Protein Aggregation

Inhibition of peptide and protein aggregation is crucial for the physical stability and safety, particularly for pharmaceutics for injection (injectabilia). Therefore, surfactants are normally applied as inhibitors of peptide and protein aggregation in such formulations. The ability, of a $C_{16}G_{8/14}$ mixture to inhibit peptide and protein aggregation in solution was investigated using insulin as model peptide. In the study, a $C_{16}G_{8/14}$ mixture was compared with Polysorbate 20 (a standard surfactant currently approved for injectabilia), and $C_{14}G_2$ (tetradecylmaltoside; a novel excipient purchased from Anatrace (Affymetrix) recently suggested for this application by Aegis Therapeutics, see [21, 22]. In the study, the insulin concentration was 0.4 mg/ml and the surfactant concentration 1.4 mg/mi. The pH of the solutions was buffered by citrate at either pH 6.8 (accelerated conditions) or pH 7.4, The solutions were put on stability in triplicates at 25 and 40° C., and analysed by visual inspection after 2, 4, 8, and 12 weeks. The results of the study is summarised in the table in FIG. 17. As is evident, $C_{14}G_2$ proved unable to inhibit precipitation, even under non-accelerated conditions. Polysorbate 20 performed considerably better, but did not stop precipitation at 40° C. at either pH 6.8 or pH 7.4. Of the three surfactants in the study, the $C_{16}G_{8/14}$ mixture proved superior. For this surfactant composition, precipitation was observed only for the most accelerated condition (40° C., pH 6.8).

Preparation of Suspensions (Dispersions; Sols)

The propensity of selected surfactant compositions to act as efficient dispersants for micronised, hydrophobic particles was tested in pharmaceutical formulations using the two steroid drugs budesonide and beclometasonedipropionate (BDP) as model compounds. The following novel alkylglycoside compositions were included in the studies: $C_{12}G_{8/14}$, $C_{16}G_{8/14}$, and $C_{16-18}G_{4-20}$. These compositions were compared with the conventional alkylglycoside compositions TEGO Care CG90 (consisting mainly of $C_{16-18}G_1$), $C_{16-18}G_{1-3}$, and $C_{16}G_2$.

In addition, the performance of the novel compositions was compared with that of the ethoxylated surfactant polysorbate 80 (PS80). PS80 used in the study was of Super-Refined grade, which represents the state-of-the-art of current technology.

The test suspensions were prepared as follows: The appropriate surfactant was dissolved in water to a concentration of 20 mg/ml. To the beaker containing the surfactant solution, an amount of drug powder was added, so that the nominal drug concentration was 50 mg/ml. The drug was then dispersed in the surfactant solution using either (1) high-shear mixing by means of an Ultra Turrax mixing device, or (2) low-shear mixing using a magnetic stirring bar. After 1 minute of agitation with either of the mixing devices, the resulting suspension was transferred to a volumetric flask and diluted 100-fold by addition of 0.15 M NaCl. Consequently, the final drug concentration was 0.5 mg/ml, and the final surfactant concentration 0.2 mg/ml.

Figure 5:
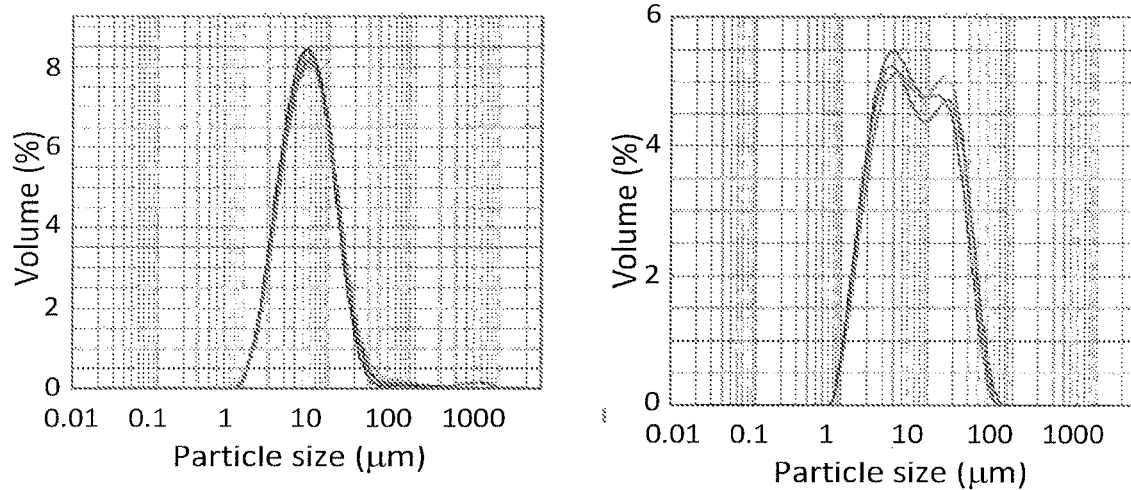
FIG. 5 shows data on particle size distributions of BDP dispersed by low-shear mixing in aqueous vehicles comprising 0.2 mg/ml of a $C_{16}G_{8/14}$ mixture (left hand panel), or comprising 0.2 mg/ml of PS80 (right hand panel).
Figure 6:
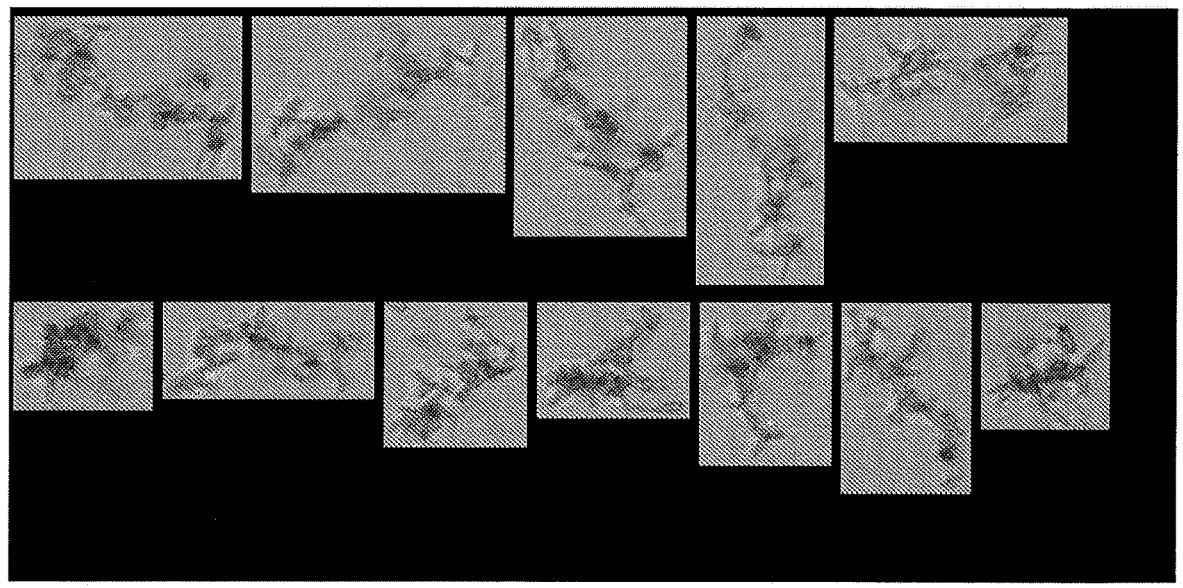
FIG. 6 shows aggregates of BDP primary particles, as characterised by Fast Particle Image Analysis (FPIA) on a system containing 0.2 mg/ml of PS80 as dispersant, and prepared by high-shear mixing.
Figure 7:
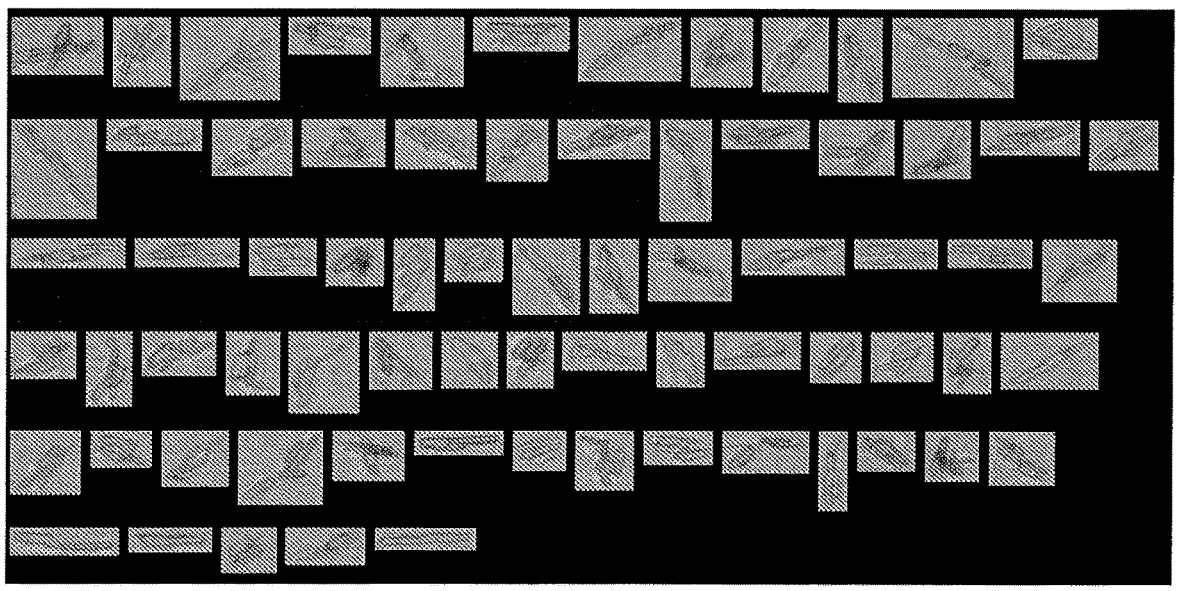
FIG. 7 shows aggregates of BDP primary particles, as characterised by FPIA analysis on a system containing a surfactant composition comprising 0.2 mg/ml of a $C_{16}G_{8/14}$ mixture as dispersant, and prepared by high-shear mixing.
Figure 8:
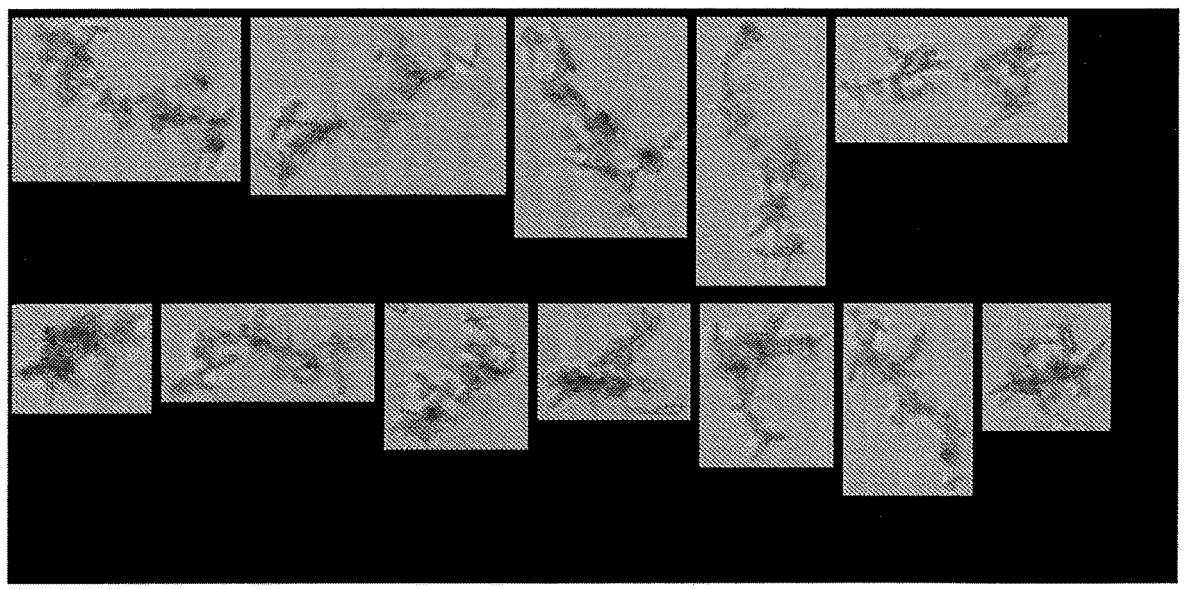
FIG. 8 shows aggregates of BDP primary particles, as characterised by FPIA analysis on a system containing 0.2 mg/ml of PS80 as dispersant and prepared by low-shear mixing.
Figure 9:
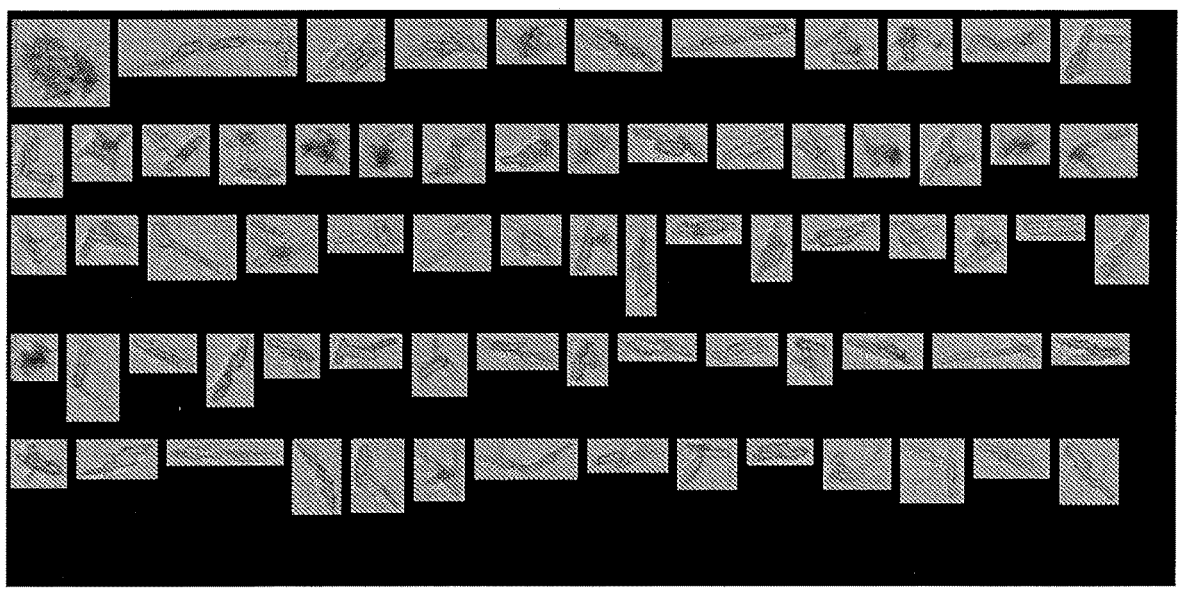
FIG. 9 shows aggregates of BDP primary particles, as characterised by FPIA analysis on a system containing a surfactant composition comprising 0.2 mg/ml of a $C_{16}G_{8/14}$ mixture as dispersant and prepared by low-shear mixing.

The two BDP suspensions containing $C_{12}G_{8/14}$ and $C_{16}G_2$ were macroscopically inhomogenous irrespective of the mode of mixing, and contained large aggregates clearly visible by the naked eye. Visible inspection thus proved sufficient to show that these surfactant compositions are useless for the intended purpose, and the suspensions were not subjected to further characterisation. The BDP suspensions containing $C_{16}G_{8/14}$ and PS80, on the other hand, were found to be homogenous to the naked eye, and were therefore subjected to further, detailed analysis by laser diffraction (Malvern MasterSizer) and fast particle image analysis (Malvern FPIA3000). As is evident from the laser diffraction data displayed in FIG. 4, use of PS80 as dispersant under high-shear conditions results in a skew-symmetric particle size distribution, clearly indicative of aggregation. Use of a $C_{16}G_{8/14}$ mixture, on the other hand, gives rise to a nearly perfect symmetrical distribution with no signs of aggregation. FIG. 5 shows the corresponding data for systems prepared by low-shear mixing. Due to the low shear, aggregates were found to be abundant in this experiment. However, there was still a huge difference between $C_{16}G_{8/14}$ and PS80. In the former case, the presence of aggregates is evident as ripples in the large-size tail of the diffraction data. However, the small size of these ripples strongly suggests that the amount of aggregates is very low. In the PS80 case, on the other hand, the size distribution function displays a pronounced bimodality, clearly suggesting a much more extensive aggregation. The conclusions derived from the laser diffraction data are confirmed and extended by the data from the image analysis. These data (in the form of micrographs of aggregates and primary particles, FIGS. 6-9) show that replacing PS80 with a $C_{16}G_{8/14}$ mixture, allows for replacing high-shear mixing with low-shear mixing, without sacrificing proper dispersion. This represents a huge advantage in a process setting, since high-shear mixing leads to substantial foaming, and concomitant issues pertaining to yield and reproducibility. The images displayed in FIGS. 6-9 have been selected so that they represent a population that is statistically representative of the largest objects (aggregates/particles) in the systems. It is important to realise that the aggregates on the two cases are very different: In the PS80 case, the aggregates are fractal objects of loosely bound primary particles, whereas in the case of a $C_{16}G_{8/14}$ mixture they are actually composed of primary particles that are fused together. The former type of aggregates are possible to disperse with a sufficiently active dispersant, whereas the latter are not (they stem from the crystallisation step in API production and are hence present in the starting material used in preparation of the suspensions). Consequently, the images in FIGS. 6-9 provide another proof that $C_{16}G_{8/14}$ is a more efficient wetting agent (dispersant) than PS80.

The ability of polydisperse alkylglycoside compositions ($C_{16-18}G_{4-20}$) to act as efficient dispersants was investigated by the same experimental protocol, but micronised budesonide as model drug. Again, the suspensions were characterized by means of laser diffraction.

Figure 10:
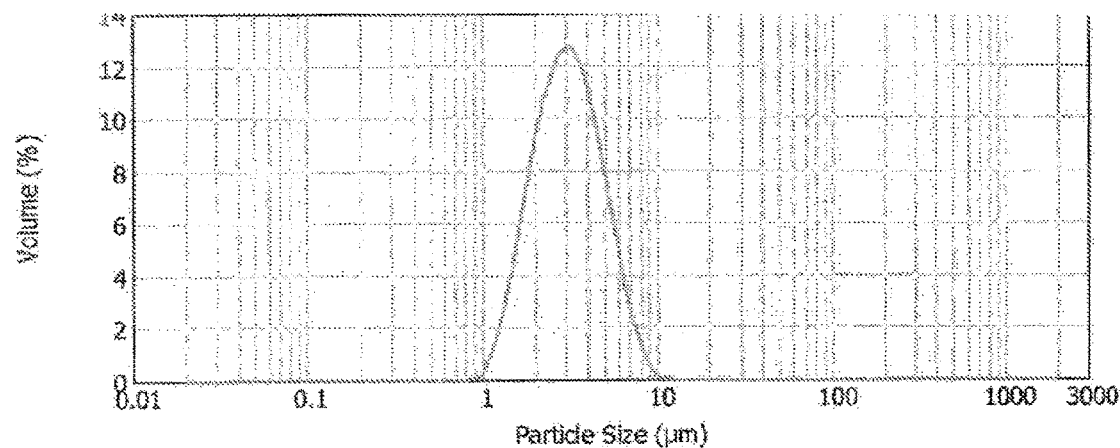
FIG. 10 shows laser diffraction data on suspensions of micronised budesonide (0.5 mg/ml), prepared with 0.2 mg/ml of $C_{16\text{-}18}G_{4\text{-}20}$ as dispersing agent.
Figure 11:
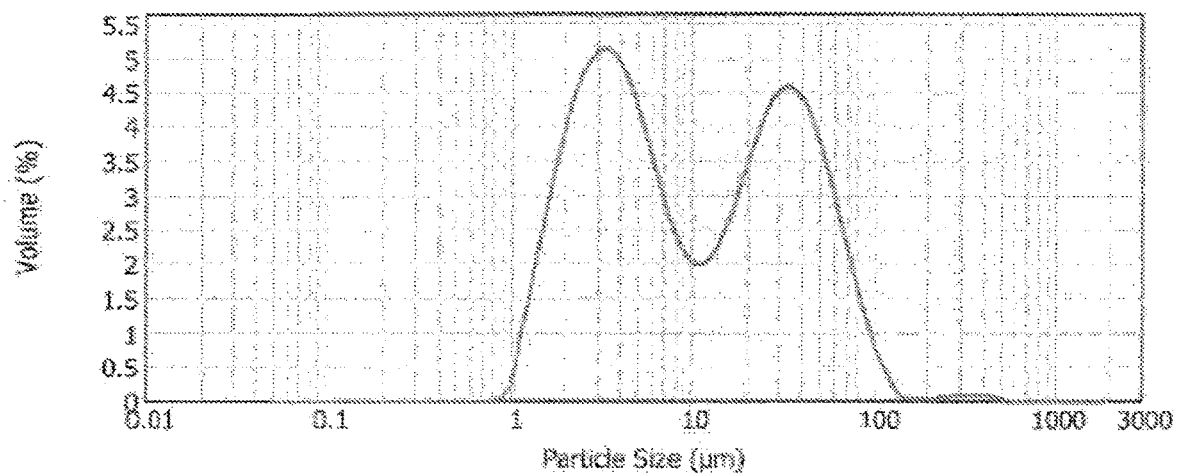
FIG. 11 shows laser diffraction data on suspensions of micronised budesonide (0.5 mg/ml), prepared with 0.2 mg/ml of $C_{16\text{-}18}G_{1\text{-}3}$ as dispersing agent.
Figure 12:
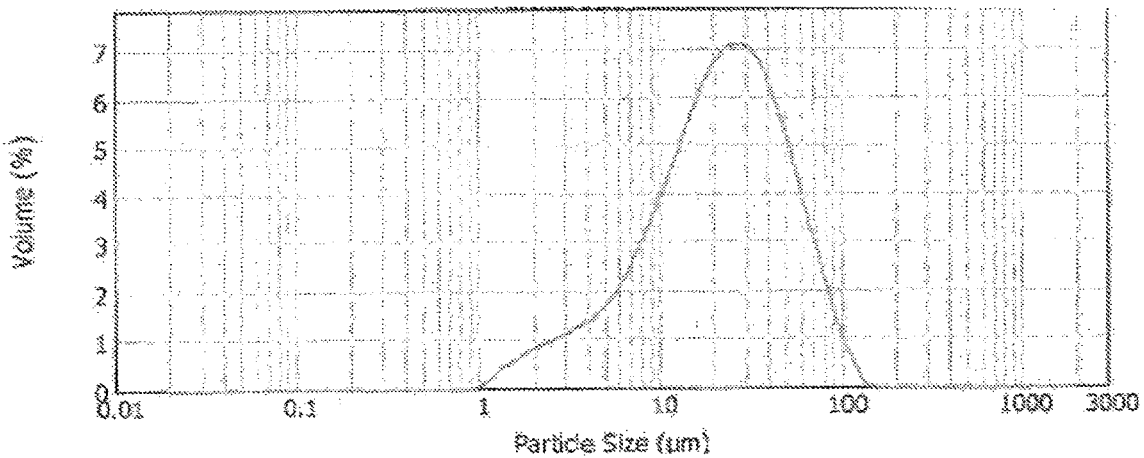
FIG. 12 shows laser diffraction data on suspensions of micronised budesonide (0.5 mg/ml), prepared with 0.2 mg/ml of TEGO Care CG90 ($C_{16\text{-}18}\,G_1$) as dispersing agent.

FIGS. 10, 11 and 12 show the laser diffraction data for budesonide suspensions containing $C_{16-18}G_{4-20}$, $C_{16-18}G_{1-3}$ and TEGO Care CG90 (consisting mainly of $C_{16-18}G_1$) as dispersant, respectively. As can be seen in FIG. 10, the particle size distribution obtained when using $C_{16-18}G_{4-20}$ as dispersant is perfectly symmetric and monomodal. This clearly shows that the system comprises only properly dispersed primary particles, and thus proves the excellent wetting properties of $C_{16-18}G_{4-20}$. In stark contrast, the distribution obtained when using $C_{16-18}G_{1-3}$ as dispersant (FIG. 11) is markedly bimodal, suggesting poor wetting and quite substantial aggregation. For TEGO Care CG90, the situation is even worse, as shown in FIG. 12. Here, only aggregates, and no primary particles, are evident in the diffraction data. In conclusion, the results clearly illustrate the importance of head-group length on surfactant performance, and also show the superiority of alkylglycosides with more than three repeating glucose units.

Heat-Stability of Suspensions

The heat stability of suspensions prepared with a surfactant composition according to the present invention was investigated by heating suspensions of micronised budesonide (0.5 mg/ml) to 90° C. for 30 minutes on a water bath and to 125° C. for 8 minutes in an autoclave. The suspensions were prepared by high-shear mixing as previously described, using 0.2 mg/ml of a $C_{16}G_{8/14}$ mixture as dispersant. The particle size distribution was investigated by means of laser diffraction measurements. For comparison, suspensions of micronised budesonide were also prepared using Polysorbate 80 as dispersant.

Figure 13:
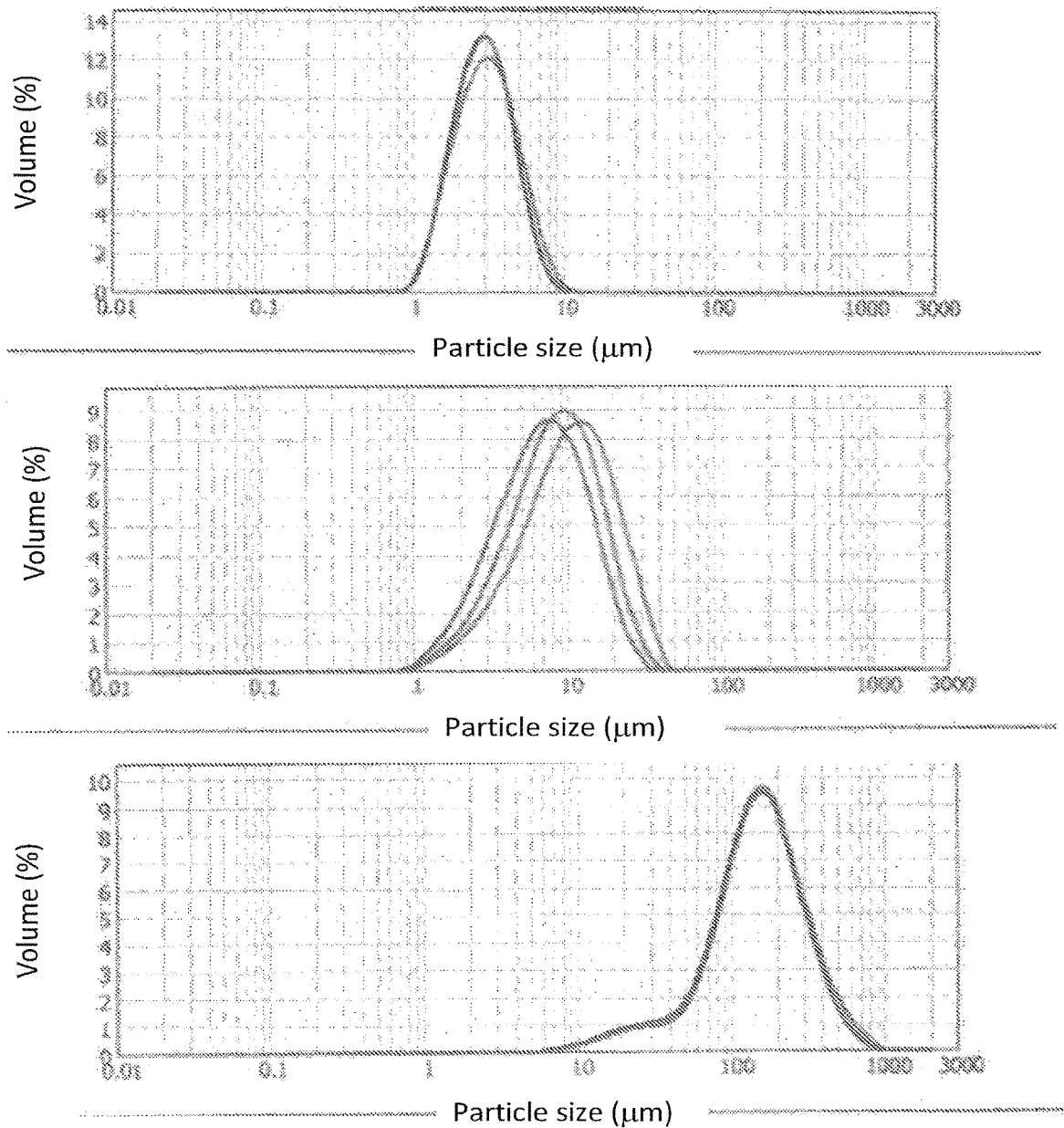
FIG. 13 shows laser diffraction data on suspensions of micronised budesonide (0.5 mg/ml), prepared with 0.2 mg/ml of Polysorbate 80 as dispersing agent. The top panel displays the particle size distribution of the suspension when freshly prepared. The middle panel displays the particle size distribution after heating to 90° C. for 30 minutes. The bottom panel displays the particle size distribution after autoclavation at 125° C. for 8 minutes.
Figure 14:
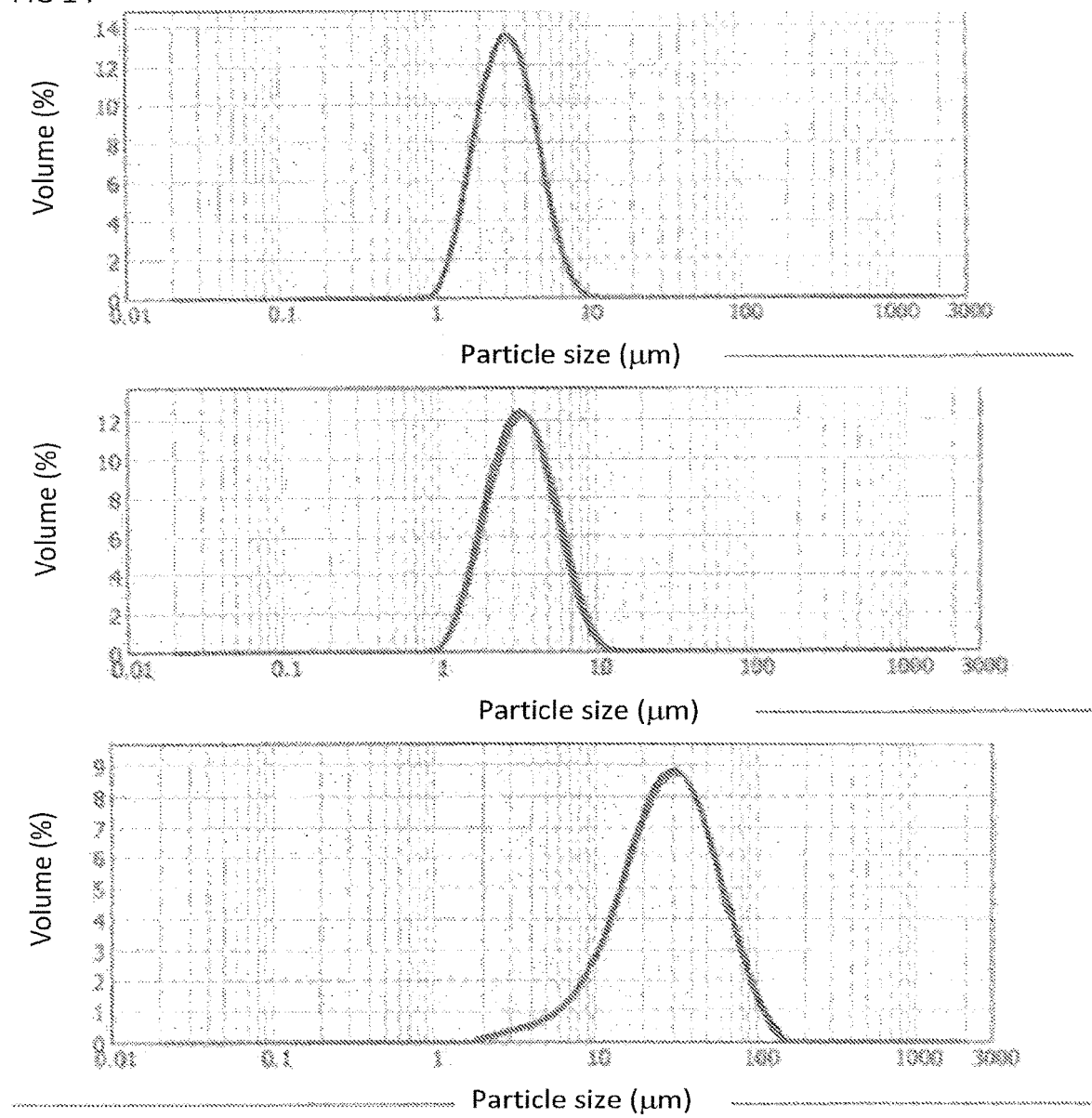
FIG. 14 shows laser diffraction data on suspensions of micronised budesonide (0.5 mg/ml), prepared with 0.2 mg/ml of a $C_{16}G_{8/14}$ mixture as dispersing agent. The top panel displays the particle size distribution of the suspension when freshly prepared. The middle panel displays the particle size distribution after heating to 90° C. for 30 minutes. The bottom panel displays the particle size distribution after autoclavation at 125° C. for 8 minutes.

Data on the particle size distribution for suspensions prepared using Polysorbate 80 as dispersant are shown in FIG. 13. As is evident, heating of the suspension to 90° C. induces a substantial shift of the particle size distribution towards higher particle size. The data demonstrate that the heat decreases the ability of Polysorbate to act as a dispersant and hence induces aggregation of primary particles. This observation is entirely consistent with the general propensity of PEG-based surfactant to phase separate at elevated temperatures, [6] and constitute, as already alluded to, a serious drawback. Under the still more severe conditions represented by autoclavation, the aggregation is near-complete and a visual inspection of the system revealed millimetre-sized chunks of aggregated budesonide that were impossible to re-disperse and that quickly settled in the bottom of the flask. Data on the particle size distribution for suspensions prepared using a $C_{16}G_{8/14}$ mixture as dispersant are shown in FIG. 14. As is evident, heating to 90° C. for 30 minutes has only minute impact on the particle size distribution. This clearly demonstrates superiority over Polysorbate 80 in terms of heat-stability. After autoclavation, the particle size distribution was found to shift substantially towards larger particle size, but still in a far less dramatic way than for the suspension prepared with Polysorbate 80. In addition, visual inspection of the suspension prepared with a $C_{16}G_{8/14}$ mixture revealed that the suspension was readily re-dispersed after autoclavation, in contrast to the suspension prepared with Polysorbate 80 as dispersant. Use of a surfactant composition according to the present invention therefore opens the possibility to utilise autoclavation as a means of sterilisation.

Preparation of Emulsions

In order to compare emulsion characteristics model emulsions containing 1.2% emulsifier (a $C_{16}G_{8/14}$ mixture; Polysorbate 80; or a $C_{12}G_{8/14}$ mixture) and 20 or 50% canola oil were manufactured. An emulsifier stock solution with a concentration of 24 mg/ml was prepared. Then, 1 ml of the stock solution was mixed with 0.6 ml of water and added to 0.4 ml canola oil to produce the 20% oil emulsions. Further, 1 ml of the stock solution was mixed with 1 ml of canola oil to produce the 50% oil emulsions. The homogenization was carried out using a SONICS, Vibracell, ultrasonic probe at 40% amplitude for 15 s, followed by a 15 s pause, for a total of 1 min active sonication. This sequence was repeated two more times with a longer break in between repetitions to minimize temperature fluctuations. This procedure resulted in smooth, white emulsions for the emulsifiers Polysorbate 80 and the surfactant composition comprising a $C_{16}G_{8/14}$ mixture. Two batches of the $C_{16}G_{8/14}$ mixture were tested and for the first two months all emulsions were stable. However, after approximately three months phase separation in the emulsions containing Polysorbate 80 and one of the $C_{16}G_{8/14}$ batches had occurred. It can therefore be concluded that a $C_{16}G_{8/14}$ mixture produces more stable emulsions than Polysorbate 80. For the $C_{12}G_{8/14}$ mixture only half the volumes listed above were used and still an additional 15 s of ultra-sonication at 70% amplitude was needed to produce smooth, white, stable (at least for three weeks) emulsions. Clearly the $C_{12}G_{8/14}$ composition is a less effective emulsifier than both the $C_{16}G_{8/14}$ composition and Polysorbate 80.

REFERENCES

1. K. Ekelund et al, J. Pharm. Sci. 2005, 94, 730.
2. M. Bergh et al, Contact Dermatitis 1998, 39, 14.
3. M. Donbrow et al, J. Pharm. Sci. 1978, 67, 1676.
4. F. O. Ayorinde et al, Rapid Comm. Mass Spectosc. 2000, 14, 2116.
5. B. A. Kerwin, J. Pharm. Sci. 2008, 97, 2924.
6. B. Jönsson et al, Surfactants and Polymers in Aqueous Solution, Wiley 1998, p. 91.
7. R. Eskuchen et al, "Technology and Production of Alkylglycosides", in "Alkyl Polyglycosides—Technology, Properties and Applications", VCH (Weinheim), 1996
8. WO2010097421
9. D. Svensson et al, Biotech. Bioeng. 2009, 104, 854.
10. D. Svensson et al, Green Chem. 2009, 11, 1222.
11. C. A. Ericsson et al, Phys. Chem. Chem. Phys. 2005, 7, 2970.
12. C. Hansson, Structure and Thermodynamics of Micellar Alkylglycoside Solutions, Diploma Work, Lund University, 2001.
13. L. Ericsson, Solid-State Phase Behaviour of Alkylglycosides, Diploma Work, Lund University, 2005.
14. B. Jönsson et al, Surfactants and Polymers in Aqueous Solution, Wiley 1998, p. 38.
15. Tween 80 Product Information Sheet, Sigma-Aldrich.
16. C. A. Ericsson el al, Langmuir 2005, 21, 1507.
17. S. H. Mollman et al, Pharm. Res. 2005, 22, 1931.
18. M. J. Rosen et al, J. Surf. Detergents 1999, 2, 343.
19. M. J. Rosen et al, Environmental Sci. Techn. 2001, 35, 954.
20. Final Safety Assessment of Decyl Glucoside and Other Alkyl Glycosides as Used in Cosmetics. Cosmetic Ingredient Review. Dec. 19, 2011.
21. WO2010151703 A1
22. EP2457580 A1
23. M. T. Gamia et al, Chemosphere 1997, 35(3), 545-556.
24. F.-X. Reichl et al, Archives of Toxicology, 2006, 80(6), 370-378.
25. Scudiero, D. A., et al., Cancer Res, 1988, 48(17), 4827-4833.

The invention claimed is:

1. A surfactant composition comprising:
   at least one alkylglycoside represented by the formula: $C_nG_{7-8}$; and
   at least one alkylglycoside represented by the formula $C_nG_{13}$,
   wherein:
   C is an alkyl group which is unbranched or branched, saturated or unsaturated;
   n is the number of carbon atoms in the alkyl group and is 14 to 24; and
   G is a saccharide residue containing 5 to 6 carbon atoms.

2. The surfactant composition of claim 1, wherein the alkyl group includes cyclic groups.

3. The surfactant composition of claim 1, wherein n is 16-18.

4. The surfactant composition of claim 1, wherein n is 16 or 18.

5. The surfactant composition of claim 1, wherein n is 18.

6. The surfactant composition of claim 1, wherein n is 14 to 20.

7. The surfactant composition of claim 1, wherein each of the alkylglycosides has a surface tension value at or above a critical micelle concentration (CMC) of at least 32 mN/m.

8. A detergent composition comprising the surfactant composition of claim 1.

9. A wetting agent comprising the surfactant composition of claim 1.

10. An emulsifying agent comprising the surfactant composition of claim 1.

11. A dispersant composition comprising the surfactant composition of claim 1.

12. An anti-aggregation and stabilizing composition comprising at least one biomolecule and the surfactant composition of claim 1.

13. A food, beverage, pharmaceutical, cosmetic, personal care product, detergent or cleaning agent comprising the surfactant composition of claim 1.

14. A method comprising incorporating the surfactant composition of claim 1 into a food, beverage, pharmaceutical, cosmetic, personal care product, detergent or cleaning agent.

15. A method of providing at least one of a detergent, wetting agent, emulsifying agent, anti-aggregation or dispersant effect to a composition comprising incorporating the surfactant composition of claim 1 into the composition.

* * * * *